(12) United States Patent
Otterson

(10) Patent No.: US 7,103,920 B1
(45) Date of Patent: Sep. 12, 2006

(54) SUNSHADE FOR A CAP

(76) Inventor: Randall Frederick Otterson, 341 Highway 311, North River, Nova Scotia (CA) B2N 5B4

(*) Notice: Subject to any disclaimer, the term of this patent is extended or adjusted under 35 U.S.C. 154(b) by 0 days.

(21) Appl. No.: 11/184,434

(22) Filed: Jul. 19, 2005

(51) Int. Cl.
A42B 1/24 (2006.01)

(52) U.S. Cl. .................. 2/209.13; 2/195.1; 2/109.12

(58) Field of Classification Search ............... 2/195.1, 2/10, 209.13
See application file for complete search history.

(56) References Cited

U.S. PATENT DOCUMENTS

| | | | |
|---|---|---|---|
| 911,432 A | 2/1909 | Pachner | |
| 1,108,649 A * | 8/1914 | Williams | 2/10 |
| 1,232,812 A | 7/1917 | Kirchner | |
| 1,735,705 A | 11/1929 | Wittcoff | |
| 1,829,538 A | 10/1931 | Prichard | |
| 1,955,232 A | 4/1934 | Gallaway | |
| 3,035,270 A * | 5/1962 | Boerner | 2/10 |
| 4,852,186 A * | 8/1989 | Landis | 2/9 |
| 5,125,113 A * | 6/1992 | Yun | 2/10 |
| 5,208,916 A | 5/1993 | Kelman | |
| 5,261,124 A | 11/1993 | Day | |
| 5,491,841 A | 2/1996 | Valletta | |
| 5,544,361 A * | 8/1996 | Fine et al. | 2/10 |
| 5,669,071 A * | 9/1997 | Vu | 2/10 |
| 6,088,837 A * | 7/2000 | Baker | 2/195.1 |
| 6,584,614 B1 * | 7/2003 | Hogg | 2/10 |
| 6,662,371 B1 * | 12/2003 | Shin | 2/10 |
| 6,739,718 B1 | 5/2004 | Jung | |

FOREIGN PATENT DOCUMENTS

CA 107754 7/2004

* cited by examiner

Primary Examiner—John J. Calvert
Assistant Examiner—Richale L. Haney
(74) Attorney, Agent, or Firm—Palmer C. DeMeo

(57) ABSTRACT

A sunshade for use with a cap is made from a thin, tinted, resilient plastic sheet which is attached to the underside of a cap's visor by means of a duck-bill or semi-moon shaped support. The sunshade has an elongated minor segment and an elongated major segment with a seam or crease dividing the two segments. The major segment can be flipped downwardly to protect the eyes of the cap's wearer from the sun's rays. The seam or crease acts as a hinge between the minor and major segments.

28 Claims, 3 Drawing Sheets

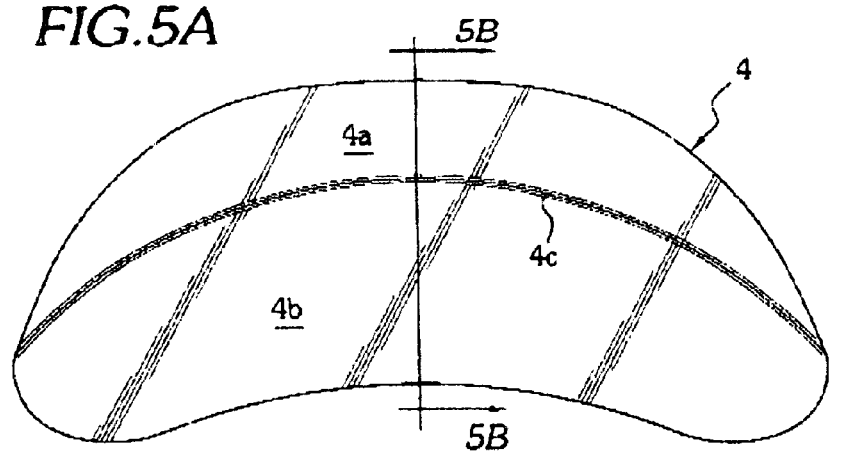
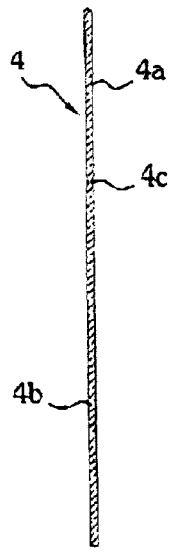
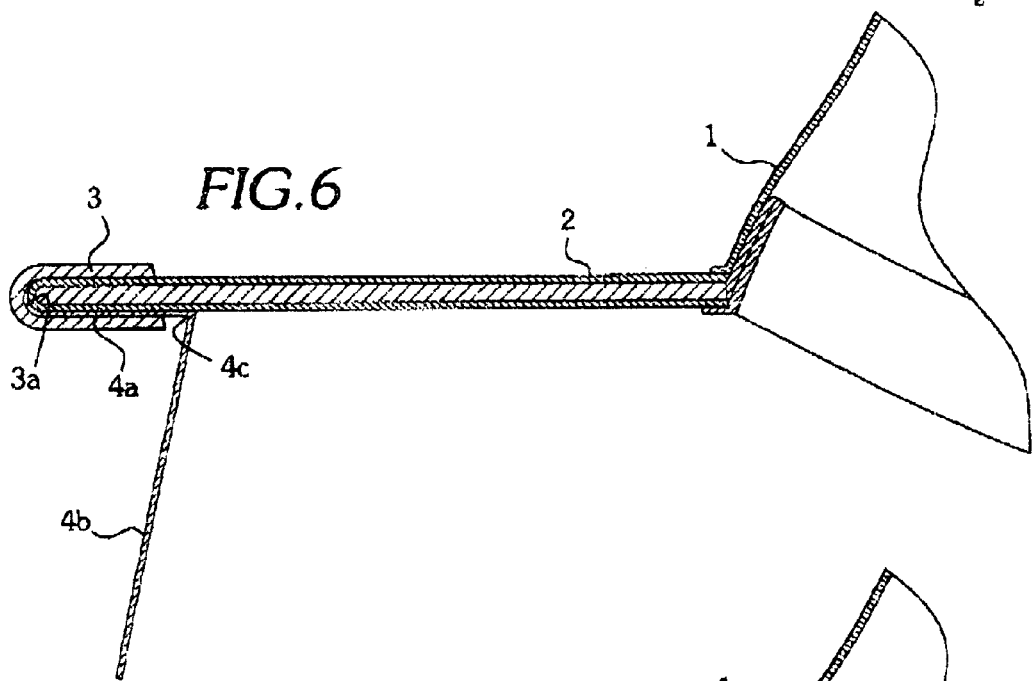
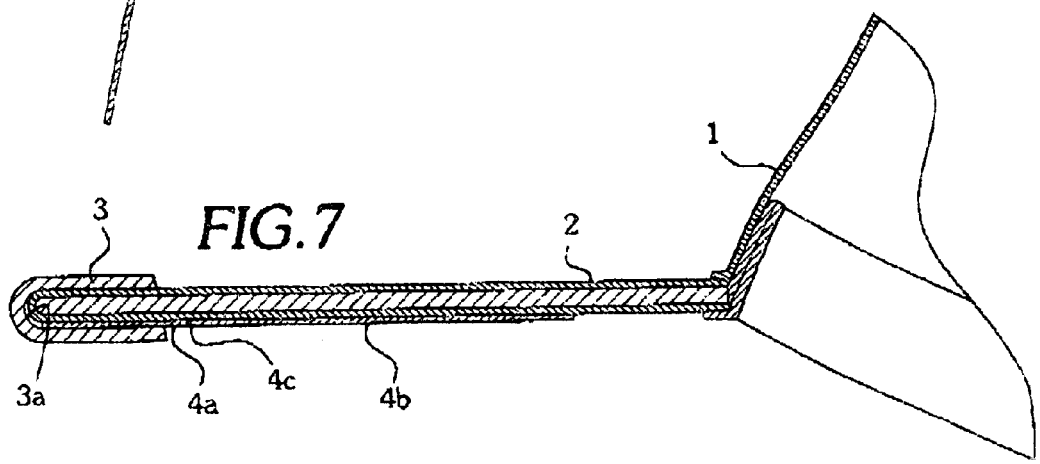

SUNSHADE FOR A CAP

BACKGROUND OF THE INVENTION

1. Field of the Invention

The present invention relates to removable sun shades for hats and caps, in general, and baseball caps, in particular.

2. Description of the Related Art

There have been numerous prior art methods for attaching a sun shade to the peripheral rim of a hat or to the visor of a baseball cap in order to obstruct or prevent the rays of the sun from striking the eyes of a wearer of the hat or cap. Many of these methods involved the use of plastic as a sunshade or sunglasses which is attached to the rim or visor by some mechanical means such as with metal hinges or clips or by sewing a part of the sun shade into the hat or cap itself. The prior art device disclosed by Jung in U.S. Pat. No. 6,739,718 provides openings in the underside of a thickened cap visor which openings register with slots therein whereby connector tabs on a peripheral edge of a semi-flexible sunglasses can be inserted into the slots for retaining the sunglasses to the visor. Once the sunglasses have been retained in this manner the major portion of the sunglasses can be flipped downwardly so as to protect the eyes of the wearer from the sun's rays. However, none of these prior art methods or sunglass devices provides a simple structure and method of attaching a removable sunshade or sunglasses to a hat or cap.

SUMMARY OF THE INVENTION

The main purpose of this invention is to provide a simple and easy method of attaching a sunshade or sunglasses to a hat or cap. Although the preferred embodiment is directed to a baseball cap with a visor the invention can also be readily applied to the rim of a hat. The sunshade or sunglasses which is made from a thin, resilient, plastic sheet is attached between a semi-moon shaped or duck billed, hard plastic element and the visor of a baseball cap. The plastic element has an elongated groove therein which tightly fits over the major surface of the curved edge of the cap's visor The sunshade or sunglasses is inserted between the bottom side of the cap's visor and the moon shaped or duck-bill shaped element. The sunshade or sunglasses has a seam or crease therein which acts as a hinge for flipping a major portion of the sunshade or sunglasses in a downward position so as to shield and protect the eyes of the cap's wearer.

Other objects and advantages in the use of the sunshade of this invention will become apparent upon reading the following description of which the attached drawings form a part.

BRIEF DESCRIPTION OF THE DRAWINGS

FIG. 5A is a top planar view of the sunshade of this invention.

FIG. 5B is a cross-sectional view of the sunshade of this invention taken across 5B, 5B of FIG. 5A.

FIG. 6 is a partial cross-sectional view of the cap, visor, support and sunshade in a deployed position FIG. 7 is a partial cross-sectional view of the cap, visor, support and sunshade in an undeployed or stored position.

DETAILED DESCRIPTION OF THE PREFERRED EMBODIMENTS

Figure 1:
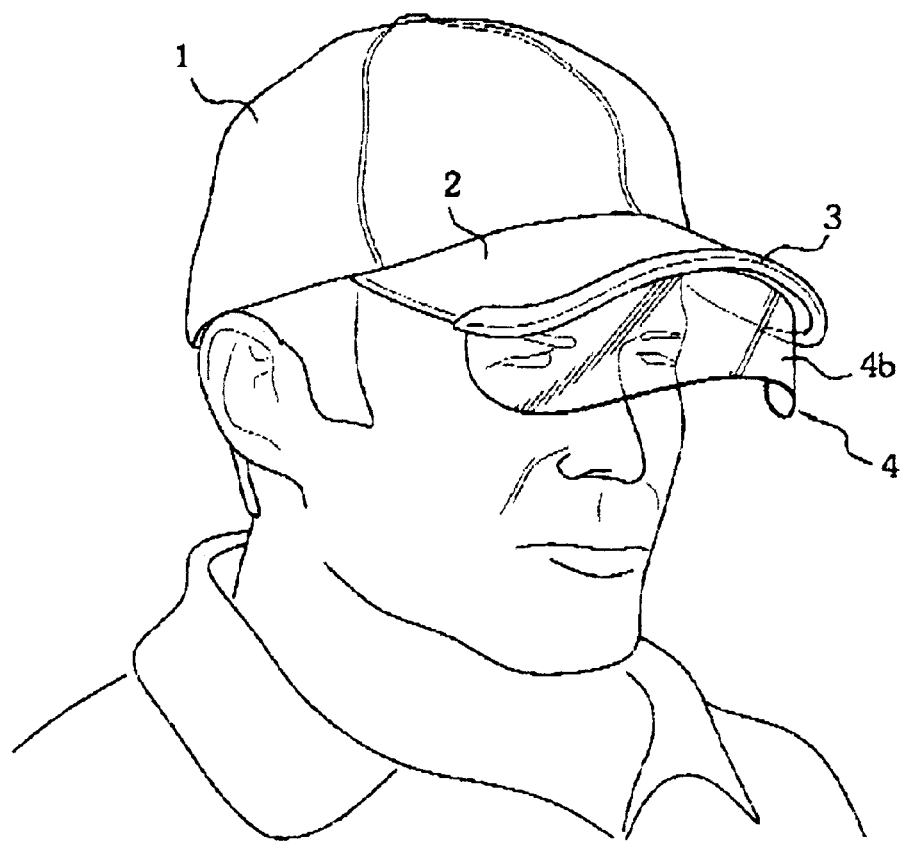
FIG. 1 is a perspective view of the sunshade of this invention in a deployed position and cap on a wearer.
Figure 2:
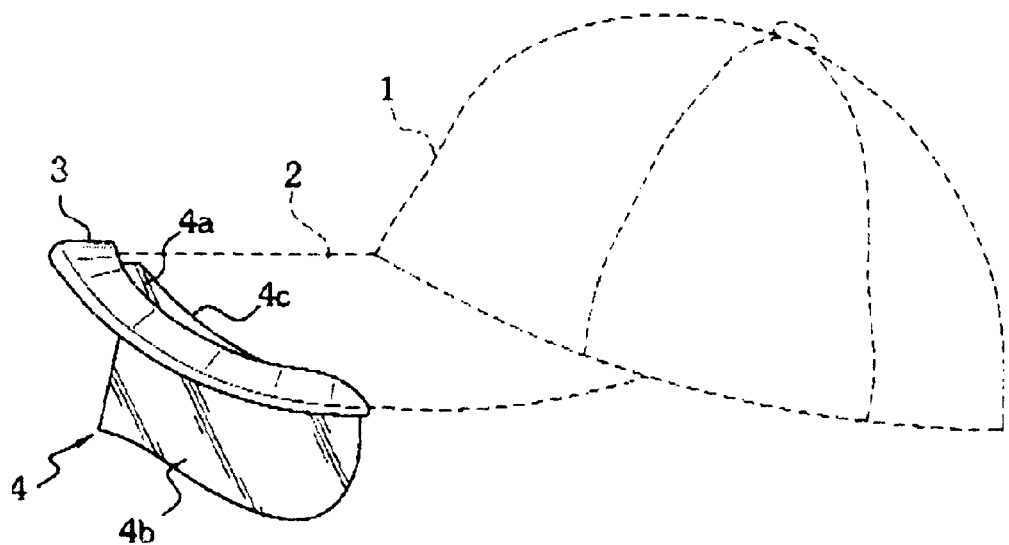
FIG. 2 is a side view of the sunshade of this invention and its holder with the sunshade in a deployed position.
Figure 3:
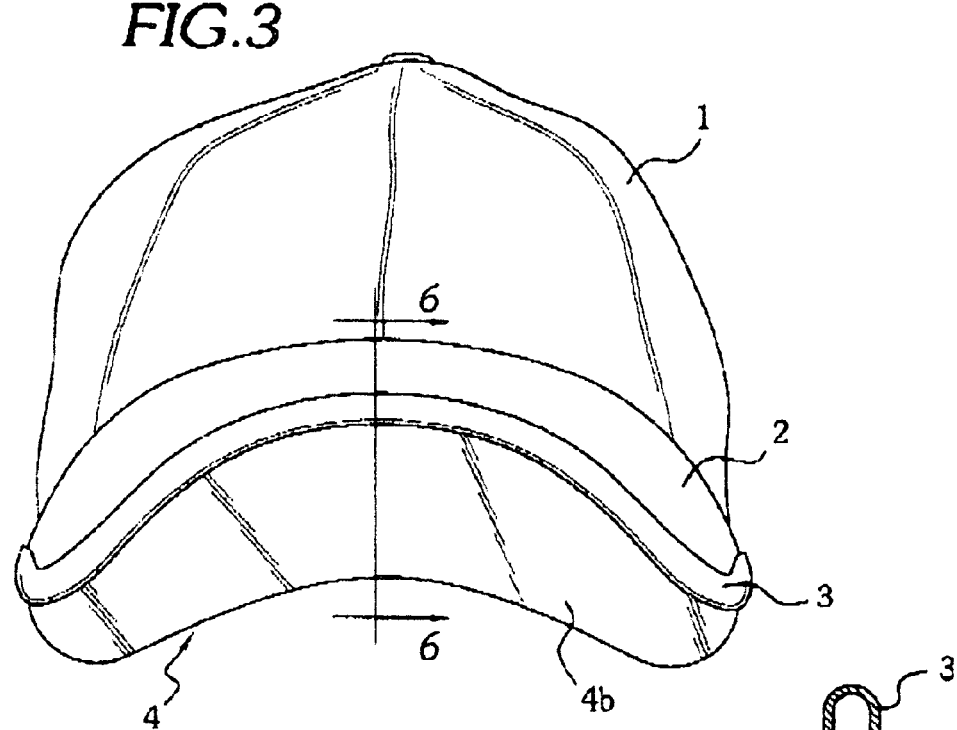
FIG. 3 is a front view of the sunshade of this invention on the visor of a baseball cap.
Figure 4C:
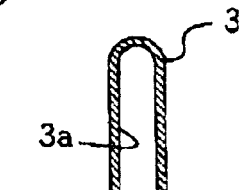
FIG. 4C is a cross-sectional view of the sunshade support taken across 4C, 4C of FIG. 4A.
Figure 4A:
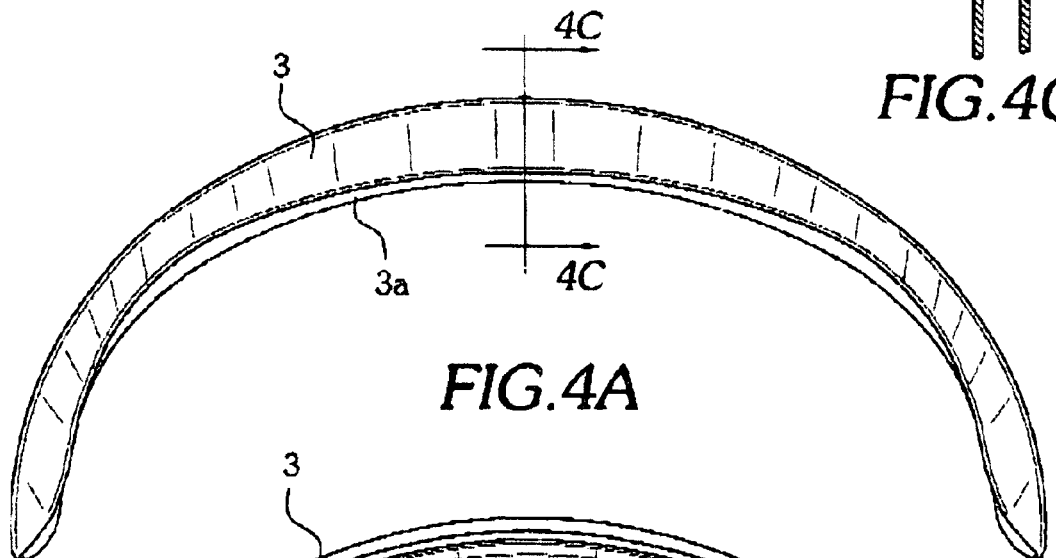
FIG. 4A is a top planar view of the sunshade support.
Figure 4B:
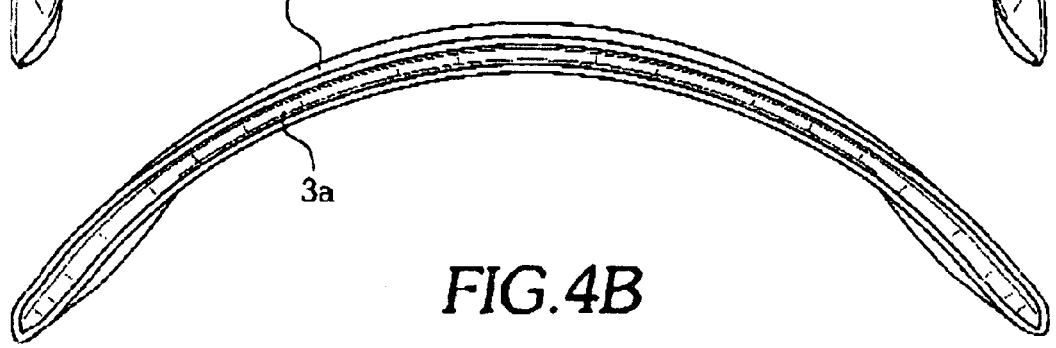
FIG. 4B is a rear elevational view of the sunshade support.

Referring to FIGS. 3A and 3b, there is shown a supporting element 3 for the sunshade 4 of this invention. Supporting element 3 has a duck billed or semi-moon shape with a groove 3a for receiving the rigid front edge of a cap visor 2. The groove 3a has a height and depth sufficient to securely hold, in a frictional engagement, the supporting element 3 to the front edge of the cap's visor 2. The length and width of the supporting element 3 as well as its curvature will depend on the dimensions of the cap's visor 2. A typical example would be: an end to end or tip to tip length of approximately 6 inches and a maximum width of approximately ¾ inch at its center. The supporting element 3 is made from a hard plastic, e.g., fiberglass, or some similar plastic.

Referring now to FIGS. 5A and 5B, there is shown the sunshade 4 of this invention which is made from a thin plastic material and which will protect the wearer's eyes from the harmful rays of the sun and/or the distracting glare of the sun's rays. The sunshade 4 is made from a thin, tinted, resilient plastic sheet. The plastic material of the sunshade 4 is made from polycarbonate plastic, e, g, Lexan, with a UVA and UVB coating or some similar plastic. The thickness of the sunshade 4 is approximately 0.010 inch to 0.015 inch although this thickness may vary for a particular application. The dimensions of the sunshade 4 will depend in part on the dimensions of the cap's visor 2. For example, the sunshade 4 which has the general shape of a banana would have a major longitudinal length of approximately 7 inches and a width of approximately 2 and ¾ inches at its center. The sunshade 4 has a minor segment 4a and a major segment 4b which segments are divided by a seam or crease 4c. It is this seam or crease 4c which provides a link between the two adjoining segments 4a and 4b of the sunshade 4 and which will act as a hinge for deployment of the sunshade 4 in an operative position as will be explained later. The minor segment 4a has a width of approximately ⅞ inch at its center and the major segment 4b has a width of approximately 1 and ⅞ inch at its center.

In FIG. 6, there is shown a partial cross sectional view of the cap's visor 2, supporting element 3 and sunshade 4 in a stored position on the bottom side of the cap's visor 2. Obviously, when the use of the sunshade 4 is not desired it can be kept in this stored position or removed entirely from the cap's visor 2 along with the supporting element 3. Initially, in order to make use of the cap's sunshade 4, the front edge of the cap's visor 2 is inserted into and fitted properly in the groove 3a of the supporting element 3. A fairly close frictional fit of the cap's visor 2 within the groove 3a secures the supporting element 3 onto the cap's visor 2. Then, the leading edge of minor segment 4a of the sunshade 4 is inserted into and fitted between the bottom side of the cap's visor 2 and the bottom section of the supporting element 3. There is sufficient yielding between the cap's visor 2 and the supporting element 3 for the insertion of the minor segment 4a between the bottom side of the cap's visor 2 and the bottom section of the supporting element 3.

After the sunshade 4 has been inserted between the visor 2 and the supporting element 3, it will spring against the underside of the visor 2 due to the hinge-like action of the seam or crease 4c and the resiliency of the sunshade 4 as shown in FIG. 7 of the drawing. Thus, the sunshade 4 is in an undeployed position and can be stored in this condition with the cap 1 until the wearer of the cap 1 is ready to use it.

When the wearer of the cap 1 desires to use the sunshade 4, the wearer simply flips the major segment 4b of the sunshade 4 downwardly or in the deployed position as shown in FIG. 6 of the drawing. The major segment 4b of the sunshade 4 will deploy at the seam or crease 4c in a downward fixed position generally perpendicular to the cap's visor 2. When the wearer of the cap 1 no longer desires or needs the use of the sunshade 4, the wearer simply flips the major segment 4b of the sunshade 4 upwardly and it will rest against the underside of the cap's visor 2 in an undeployed condition or stored position as shown in FIG. 7 of the drawing. The seam or crease 4c of the sunshade 4 acts as a hinge whenever the major segment 4b of the sunshade 4 is flipped downwardly or upwardly.

Modification of this invention will be readily apparent to those skilled in the art and it is intended that the invention be not limited by the embodiments disclosed herein but that the scope of the invention be defined by the appended claims.

What is claimed is:

1. A sunshade for a cap having a visor, said sunshade comprising a thin plastic resilient sheet, said sunshade having a major elongated segment and a minor elongated element, said major segment having a planar width at its mid-section greater than the planar width of said minor segment at its mid-section, said major segment providing protection from the sun's rays and said major and minor segments being separated by a seam or crease extending along the entire longitudinal length between said major and minor segments wherein said seam or crease acts as a hinge for flipping said major segment perpendicularly relative to said minor segment.

2. The sunshade of claim 1 wherein an elongated holder, having a groove along its length, is attached to said visor and said sunshade is attached to said visor by means of said elongated holder.

3. The sunshade of claim 2 wherein said visor is inserted within said grooved holder and said minor elongated segment is inserted between said visor and said grooved holder.

4. The sunshade of claim 3 wherein both segments of said sunshade are stored adjacent and beneath said visor when not deployed.

5. The sunshade of claim 3 wherein said major segment is substantially perpendicular to said visor when deployed.

6. The sunshade of claim 2 wherein said holder is made from a hard plastic.

7. The sunshade of claim 6 wherein said hard plastic is fiberglass.

8. The sunshade of claim 2 wherein the length of said groove is substantially the same length as said minor elongated segment.

9. The sunshade of claim 1 wherein said thin plastic sheet is made from polycarbonate plastic.

10. The sunshade of claim 1 wherein said sunshade has a banana shaped configuration.

11. The sunshade of claim 1 wherein said plastic sheet has a UVA and UVB protective coating thereon.

12. In combination, a sunshade and holder for a cap with a visor, said visor having a curved major section with a peripheral edge, said holder being elongated and curved along its length and having an elongated groove therein to accommodate the insertion of said peripheral edge of said visor, said sunshade comprising an elongated, thin plastic resilient sheet having approximately the same length as said groove, said sunshade having an elongated minor segment and an elongated major segment with a seam or crease extending along the entire longitudinal length between said minor and major segments, said major segment providing protection from the sun's rays, said elongated minor segment being inserted between said visor and said holder, and said seam or crease acting as a hinge for flipping said major segment downwardly and perpendicularly relative to said minor segment.

13. The combination of claim 12 wherein said holder is made from a hard plastic.

14. The combination of claim 13 wherein said hard plastic is fiberglass.

15. The combination of 12 wherein the length of said groove is substantially the same length as said minor elongated segment.

16. The combination of claim 12 wherein said thin plastic sheet is made from polycarbonate plastic.

17. The combination of claim 12 wherein said sunshade has a banana shaped configuration.

18. The combination of claim 12 wherein said plastic sheet has a UVA and UVB protective coating thereon.

19. A sunshade for a cap with a visor, said sunshade comprising a resilient plastic sheet, said plastic sheet having two adjoining, elongated, planar segments separated by a seam or crease, said seam or crease extending along the entire longitudinal length between said adjoining segments, one of said segments being attached to said visor and the other of said segments being deployable relative to said one segment in order to protect the cap's wearer from the rays of the sun and said seam or crease acting as a hinge between said two adjoining elongated planar segments.

20. The sunshade of claim 19 wherein said plastic sheet has a UVA and UVB protective coating thereon.

21. A sunshade for a cap having a visor, said sunshade comprising a thin plastic resilient sheet, said sunshade having a major elongated segment and a minor elongated element, said major segment having a planar width at its mid-section greater than the planar width of said minor segment at its mid-section, said major segment providing protection from the sun's rays and said major and minor segments being separated by a seam or crease along their longitudinal lengths wherein said seam or crease acts as a hinge for flipping said major segment perpendicularly relative to said minor segment, said sunshade, said sunshade further comprising an elongated holder, having a groove along its length, that is attached to said visor and said sunshade is attached to said visor by means of said elongated holder, said visor being inserted within said grooved holder and said minor elongated segment is inserted between said visor and said grooved holder wherein both segments of said sunshade are stored adjacent and beneath said visor when not deployed.

22. The sunshade of claim 21 wherein said major segment is substantially perpendicular to said visor when deployed.

23. The sunshade of claim 21 wherein said holder is made from a hard plastic.

24. The sunshade of claim 23 wherein said hard plastic is fiberglass.

25. The sunshade of claim 21 wherein the length of said groove is substantially the same length as said minor elongated segment.

26. The sunshade of claim 21 wherein said thin plastic sheet is made from polycarbonate plastic.

27. The sunshade of claim 21 wherein said sunshade has a banana shaped configuration.

28. The sunshade of claim 21 wherein said plastic sheet has a UVA and UVB protective coating thereon.

* * * * *